United States Patent [19]

Colvin, Jr. et al.

[11] Patent Number: 4,894,152

[45] Date of Patent: Jan. 16, 1990

[54] FLUID CONTROL DEVICE

[75] Inventors: Arthur E. Colvin, Jr., Mount Airy, Md.; Matthew W. Hanley, Washington, D.C.

[73] Assignee: Cerex Corporation, Gaithersburg, Md.

[21] Appl. No.: 84,880

[22] Filed: Aug. 13, 1987

[51] Int. Cl.[4] .............................................. B01D 15/08
[52] U.S. Cl. ................... 210/198.2; 210/456; 55/386
[58] Field of Search ............ 210/656, 658, 659, 198.2, 210/510.1, 180, 188, 456; 55/386

[56] References Cited

U.S. PATENT DOCUMENTS

| 1,948,503 | 2/1934 | Bijur | 184/7 |
|---|---|---|---|
| 2,957,308 | 10/1960 | McMurtrey et al. | 60/35.6 |
| 3,440,864 | 4/1969 | Blume | 210/198.2 |
| 3,483,986 | 12/1969 | Wright | 210/232 |
| 3,487,938 | 1/1970 | Patterson | 210/198.2 |
| 3,519,024 | 7/1970 | Johnson et al. | 138/41 |
| 3,539,505 | 11/1970 | Lauer et al. | 210/31 |
| 3,678,963 | 7/1972 | Betts et al. | 138/41 |
| 3,771,659 | 11/1973 | Fraser | 210/198.2 |
| 4,061,031 | 12/1977 | Grimsrud | 210/188 |
| 4,139,469 | 2/1979 | Rainin et al. | 210/136 |
| 4,208,279 | 6/1980 | Varani | 210/180 |
| 4,228,007 | 10/1980 | Rausch | 210/198.2 |
| 4,344,459 | 8/1981 | Nelson | 138/45 |
| 4,350,595 | 9/1982 | Gunkel | 210/198.2 |
| 4,354,932 | 10/1982 | McNeil | 210/198.2 |
| 4,384,957 | 5/1983 | Crowder | 210/198.2 |
| 4,469,597 | 9/1984 | Mott | 210/198.2 |
| 4,557,830 | 12/1985 | Onitsuka | 210/198.2 |
| 4,582,608 | 4/1986 | Ritacco | 210/656 |
| 4,629,561 | 12/1986 | Shirato et al. | 210/198.2 |
| 4,636,315 | 1/1987 | Allen | 210/198.2 |
| 4,636,316 | 1/1987 | Harris et al. | 210/656 |
| 4,675,104 | 6/1987 | Rai | 210/198.2 |
| 4,676,898 | 6/1987 | Saxema | 210/198.2 |

Primary Examiner—Ernest G. Therkorn
Attorney, Agent, or Firm—Michael W. York

[57] ABSTRACT

A fluid control device for use in a fluid chromatography system comprising a control plate with a radial channel structure and a porous plug to create a fluid distribution across the entire cross sectional area of a separating matrix yielding increased efficiency in fluid chromatography operations.

7 Claims, 4 Drawing Sheets

FLUID CONTROL DEVICE

BACKGROUND OF THE INVENTION

The present invention generally relates to a fluid control device, particularly to such a device which is to be included as a component of a fluid chromatography system.

Often a substance is produced, or is found, as a component of a complex mixture. Frequently, these mixtures will include other components which are not useful or may even be harmful. Thus, it is often necessary to fractionate the complex mixture so as to separate a sub-fraction containing the desirable component.

One of the ways that complex mixtures can be fractioned is by fluid chromatography. Fluid chromatography may be briefly described as the fractionation of components of a mixture based on differences in the physico/chemical characteristics of the components. The various fluid chromatographic systems fractionate the components, in effect, based on the different reaction rates of the components with a fractionation matrix. Some fluid chromatographic matrix systems fractionate the components of a mixture based upon such physical parameters as, for example, the molecular weight. Still other fluid chromatographic systems will fractionate the components of a mixture based upon such chemical criteria as, for example, ionic charge, hydrophobicity, and the presence of certain chemical moieties such as, for example, antingenic determinants or lectin-binding sites on the components.

In order to fully realize the maximum potential of such a system it is important to utilize as much as possible of the interaction area between the fluid and the fractionation matrix. Thus, one would like to have the incoming fluid distributed across the entire cross-sectional area of the fractionation matrix. If such a distribution is not created, streaming may occur and the core of the separating matrix may become saturated such that the reactions necessary to effectuate effective component separation may not occur.

U.S. Pat. No. 4,354,932 to McNeil discloses a fluid control device comprising an apertured plate and a series of four screens to radially distribute fluid in a liquid chromatography system. U.S. Pat. No. 4,582,608 to Ritacco uses a dispenser part in combination with a wire mesh screen and a sintered stainless steel disk to spread incoming fluid over the entire cross sectional area of a chromatography column.

The present invention is able to accomplish this goal using a single, low cost fluid control plate with radially outward channels formed on one side thereof and a mechanism associated with the plate to prevent streaming of the incoming fluid.

SUMMARY OF THE INVENTION

It is an object of this invention to provide a fluid control device which creates a uniform fluid distribution across the entire cross sectional area of the separating matrix of a fluid chromatography system.

It is another object of this invention to provide a fluid control device which helps to reduce streaming of the incoming fluid in a fluid chromatography system.

It is still another object of this invention to provide a fluid control device for a fluid chromatography system with a mechanism for releasing bubbles contained in the incoming fluid.

The present invention thus relates to a fluid control device which enables the uniform delivery of fluid in a fluid chromatographic system. In so doing, maximum utilization of the matrix of the system is achieved to thereby allow high efficiency of separation and avoid localized premature saturation of the matrix.

In fluid chromatography it would be useful to direct fluid into the matrix such that the matrix is exposed to the components of the sample in a fairly uniform manner. Although devices for directing the flow of fluid into and from a fluid chromatographic matrix are known, the prior art devices have significant disadvantages associated with them not found in the devices of the invention. For example, prior art devices do not give a uniform distribution of sample at the interface between the device and the matrix. As a result, those areas of the matrix where there is greater contact with the sample experience a localized saturation effect compared to other areas of the matrix with less contact with the sample. Consequently, separation of the components of the sample quickly degenerates, resulting in loss in the ability of the matrix to resolve the components of the sample. This loss of resolution increases significantly with the increasing flow rate of a sample into the matrix, thus, creating another major disadvantage of prior art devices, namely, their inability to operate effectively at high sample flow rates. In contrast, the fluid control devices of the invention control the flow of sample into and, if desired, from the fluid chromatographic matrix such that localized premature saturation of the matrix does not occur, thus allowing higher sample flow rates.

These and other objects and advantages will become apparent from the following drawings and specification.

DETAILED DESCRIPTION OF THE INVENTION

Figure 1:
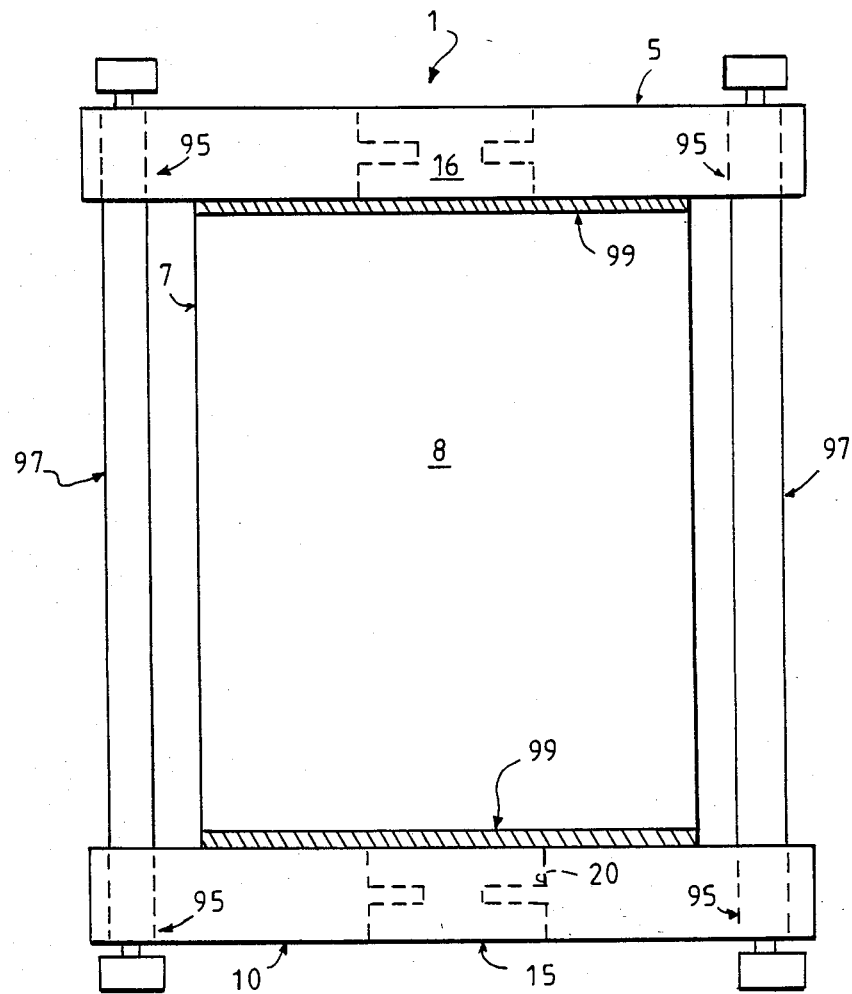
FIG. 1 is a cross-sectional view of the fluid chromatography system of this invention.

The fluid chromatography assembly 1 includes upper and lower control plates 5 and 10 and a region 7 containing separation matrix 8, as indicated in FIG. 1.

In general, a separation matrix effects a separation of the components of a mixture because of the various interaction rates between the matrix and the different mixture components. In order to ensure maximum efficiency and accuracy in the separation process, it is important that the fluid to be analyzed be distributed throughout the entire separation matrix. Control plate 10 has a network of grooves cut into one side thereof which are designed to promote such distribution.

The term "fluid chromatography" as used herein is meant to denote chromatographic systems which operate using a mobile phase, such as for example, in liquid chromatography or gas chromatography, for separation of the various components of the mixture.

Figure 2:
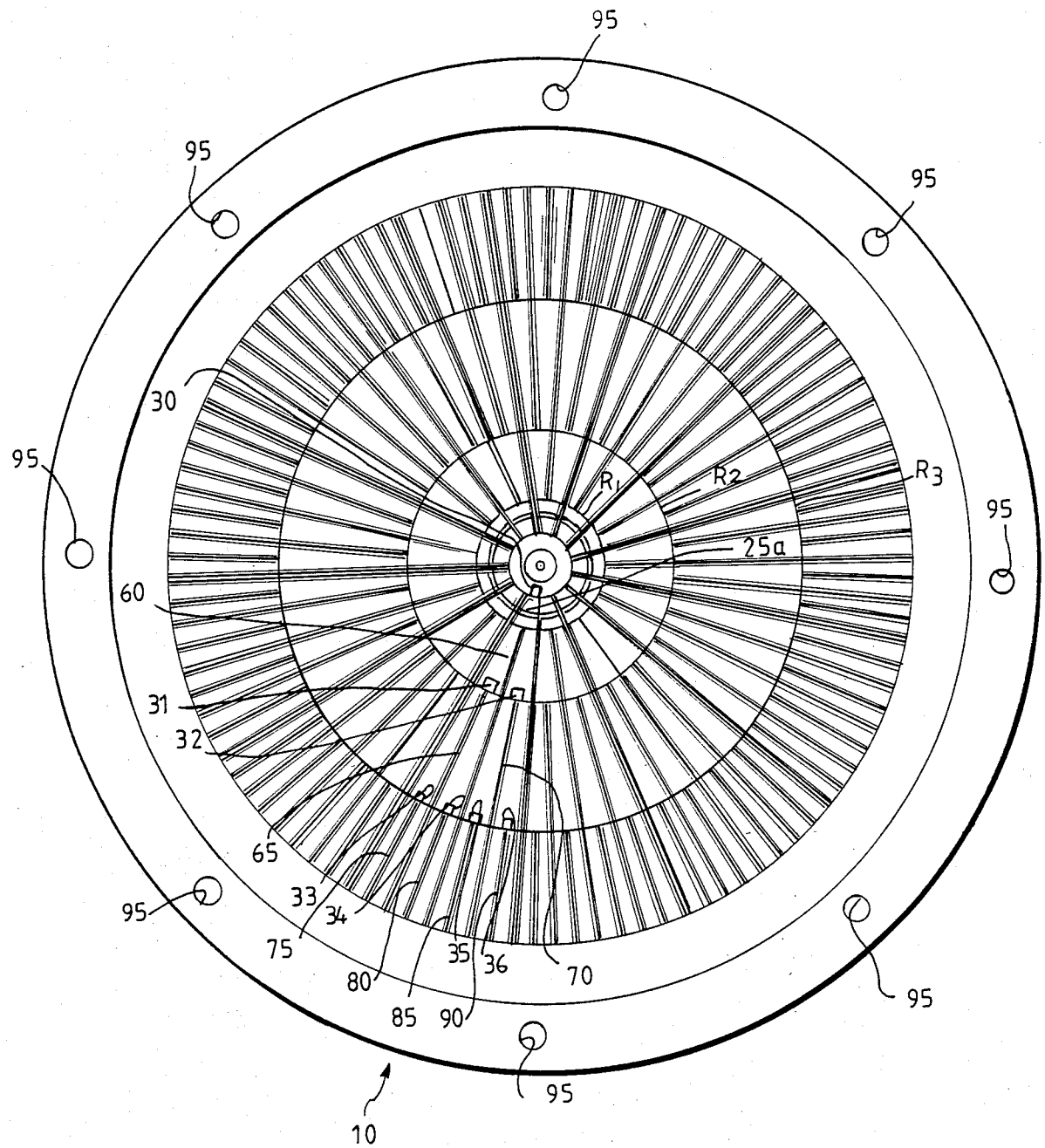
FIG. 2 is a plan view of the fluid control plate of this invention without the O-ring trough structure.

Fluid enters the chromatography system 1 through an aperture 15 centrally bored in the fluid control plate 10. Here it encounterd a porous plug 20. The plug serves several purposes. First, depending on the type of material used, the plug may serve as a prefilter to remove unwanted substances from the incoming fluid. Second, the plug serves as a fluid dispenser. It prevents the fluid from streaming through the separation matrix by helping to force the fluid into the channels 25a–n formed on control plate 10, which are best illustrated in FIG. 2. This helps to ensure that the fluid is widely distributed as it enters the separation matrix. In the embodiment described herein, the porous plug is formed of polyethylene although other suitable materials may be substituted. Porous materials useful in forming the porous plug can be polymeric or non-polymeric. Polymeric substances in addition to polyethylene such as, for example, polypropylene and teflon can also be used.

Useful non-polymeric materials for forming the porous plug include porous metals or alloys, such as porous stainless steel, as well as scintered materials, such as scintered glass and scintered stone. Those of skill in the art will know of, or can readily ascertain, other materials of which the porous plug can be composed.

Once a fluid element is forced into a channel, part of the pressure of the still incoming fluid behind it causes the element to move toward the outer edges of the plate 10. The path followed as the fluid element moves outward is clearly dependent on the channel structure cut into the fluid control plate. This structure may vary in its details, but it should be radially oriented from the central aperture 15. The embodiment described herein, and pictured in FIG. 2, is merely representative of one way to enhance the distribution of fluid across the cross-sectional area of the separation matrix.

Consider a fluid element 30 forced into a channel 25a. The fluid will begin to move radially outward and continue as such until it encounters barrier 60. At this point, the fluid element 30 will divide into sub-elements 31 and 32 respectively. Each of these subelements will continue in their respective channels until being further subdivided by barriers 65 and 70. Sub-elements 33–36 continue in their respective channels until being subdivided still again by barriers 75, 80, 85 and 90.

When such a process occurs for each of the main channels 25a–n, it will be seen that the fluid is uniformly distributed over the entire cross-sectional area of the separation matrix.

Figure 3:
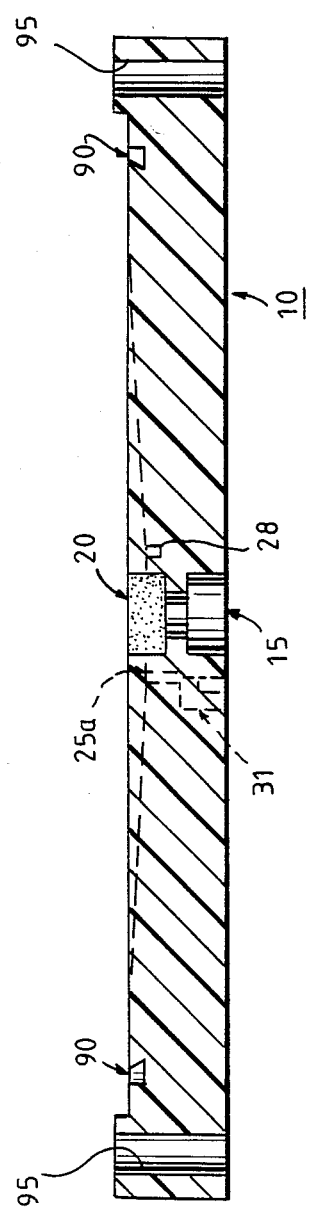
FIG. 3 is a cross sectional view of the fluid control plate of this invention.
Figure 5:
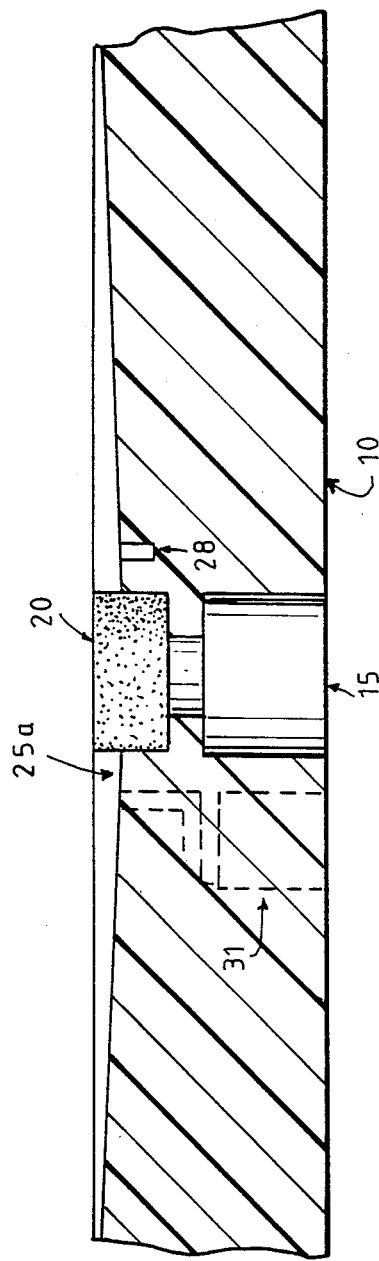
FIG. 5 is an enlarged cross sectional view illustrating the structure of the bubble trough and bubble release.
Figure 6:
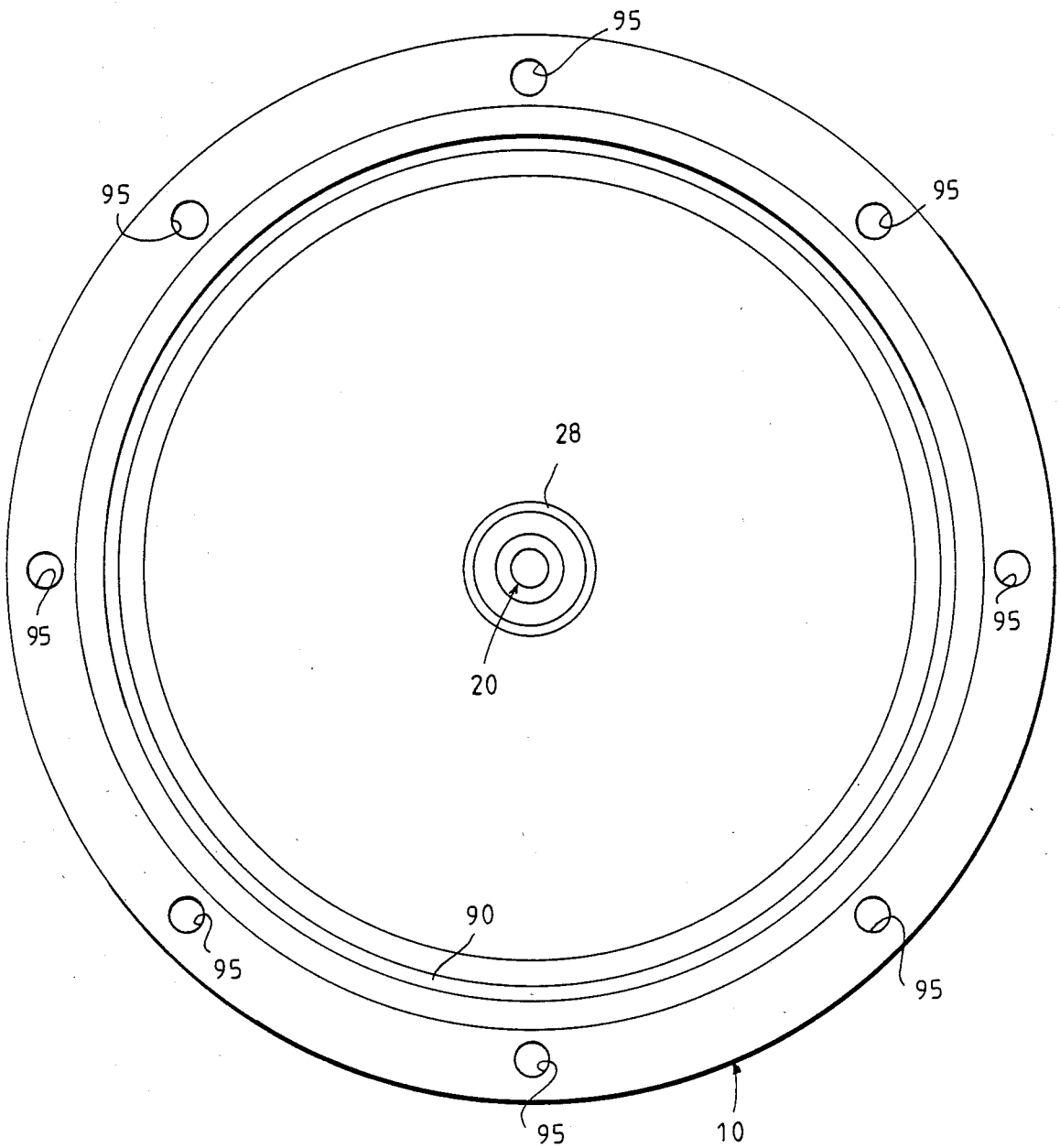
FIG. 6 is the view as in FIG. 1 illustrating the O-ring trough and without the detail of the channel structure.

The channels are further characterized by a small upward slope from the center to the outer edge of the plate, as best illustrated in FIGS. 3 and 5. This aids in the distribution as well as the introduction of the fluid into the separation matrix. The embodiment described herein has a 2° slope, but this should not be understood as limiting in any respect.

Once the fluid has travelled through the separating matrix, it encounters a second plate 5 with an aperture 16 through which the fluid may exit the chromatography system. This second plate may be identical in construction with plate 10 with the channels now serving to lead the fluid having undergone treatment toward the aperture 16. However, since the fluid has already passed through the separating matrix, one may choose to omit or vary the channel structure of the exit plate 5.

In addition to the features described above, several others may also be included.

When fluid is being pumped into the system, bubbles may be formed which may lower the effectiveness of the channelling structure. One remedy is to provide a bubble escape. This may be effected on the control plate 10 of this invention by including a circular trough 28 centered about aperture 15 and intersecting the radially oriented channels 25a–n. A second aperture 31 is bored through plate 10 permitting the release of any bubbles trapped in the trough 28, as indicated in FIG. 5.

Figure 4:
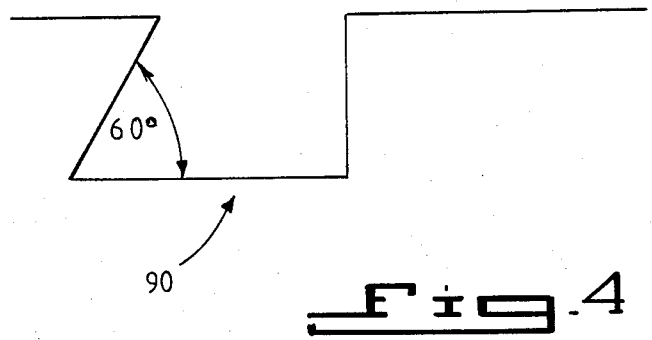
FIG. 4 is an enlarged cross sectional view of the O-ring trough with undercut.

At the outer edge of the channel structure, a second trough or groove 90 may be cut in order to retain an O-ring. This O-ring aids in the creation of an effective seal between the control plate 5 and 10 and the separation matrix 8. Groove 90 may be undercut as illustrated in FIG. 4 in order to better hold the O-ring in position.

In addition, a plurality of holes 95 may be bored in the upper and lower control plates 5 and 10 which may be used to retain an equal number of nut-bolt pairs 77 as a means of holding the chromatography system together.

If desired, a porous membrane 99 can be placed between the plate and the matrix. Such a membrane is preferred when the plate of the invention is used in conjunction with a granular or particulate matrix. The pores of the membrane should be large enough to allow efficient passage of fluid sample into the matrix, but small enough to prevent blockage of the pores of the membrane by the matrix or direct contact between the matrix and the inwardly facing plate.

While the foregoing description is directed to only a few presently preferred embodiments, it will be obvious to one of ordinary skill that numerous modifications may be made without departing from the true spirit or scope of the invention which is to be limited only by the appended claims.

What is claimed is:

1. A fluid control device for a fluid chromatography system comprising:
    a plate;
    an aperture centrally located through said plate for introducing fluid to said system;
    radially oriented channels formed in one side of said plate and radiating outward from said aperture with a slope such that the channels decrease in depth from the center portion to the outer edge portion of said plate;
    raised radial flutes located in said radially oriented channels to divide said channels into at least two radially oriented subchannels;
    structure wherein said radially oriented channels are confined to a region extending from an inner edge at the edge of said centrally located aperture in the plate to an outer edge at a predetermined radius from the center of said centrally located aperture with:
    radius $r_1$ located between said inner and outer edges;
    a first set of equally spaced, raised radial flutes extending from said inner edge to said outer edge defining a first set of channels;
    a second set of equally spaced, raised radial flutes extending from radius $r_1$ to said outer edge and being positioned so as to bisect said first set of channels into a first set of equal subchannels; and
    a porous plug located in the centrally located aperture located through said plate adjacent said radially oriented channels for helping force fluid into 2. The fluid control device of claim 1 wherein the slope of the radially oriented channels is less than five degrees.

3. The fluid control device of claim 1 further comprising:
  radius $r_2$ located between $r_1$ and said outer edge;
  radius $r_3$ located between $r_2$ and said outer edge; and
  a third set of equally spaced, raised radial flutes extending from $r_2$ to said outer edge and being positioned so as to bisect each of said first set of equal subchannels and thereby define a second set of equal subchannels;
  a fourth set of equally spaced, raised radial flutes extending from radius $r_3$ to said outer edge and being positioned so as to bisect each of said second set of equal subchannels and thereby define a third set of equal subchannels.

4. The fluid control device of claim 3 wherein said first set of raised radial flutes comprises 13 flutes.

5. The fluid control device of claim 1 wherein said fluid control device is for use with a matrix and further comprising a porous membrane located adjacent said plate having pores large enough to allow passage of a fluid sample but small enough to prevent blockage of the pores by a matrix used with said fluid control device.

6. The fluid control device of claim 1 further comprising a circular groove located in the outer portion of said plate for holding an O-ring.

7. The fluid control device of claim 6 wherein said circular groove located in the outer portion of said plate is undercut to hold said O-ring in position.

* * * * *